United States Patent [19]

Matsuo et al.

[11] Patent Number: 4,785,402
[45] Date of Patent: Nov. 15, 1988

[54] ULTRASONIC IMAGING APPARATUS FOR COLOR DISPLAY OF FLOW VELOCITY

[75] Inventors: Satoshi Matsuo, Ootawara; Yasuo Miyajima, Tochigi, both of Japan

[73] Assignee: Kabushiki Kaisha Toshiba, Kawasaki

[21] Appl. No.: 924,559

[22] Filed: Oct. 29, 1986

[30] Foreign Application Priority Data

Nov. 2, 1985 [JP] Japan .............................. 60-247796

[51] Int. Cl.$^4$ ............................................. G06F 15/42
[52] U.S. Cl. ........................... 364/413.07; 128/661.08;
364/413.25
[58] Field of Search ................ 128/660, 663; 364/416, 364/414

[56] References Cited

U.S. PATENT DOCUMENTS

| | | | |
|---|---|---|---|
| 3,773,033 | 11/1973 | Rodbard et al. | |
| 3,878,832 | 4/1975 | Tickner et al. | |
| 4,094,308 | 6/1978 | Cormier | |
| 4,159,462 | 6/1979 | Rocha et al. | |
| 4,183,046 | 1/1980 | Dalke | 358/22 |
| 4,257,278 | 3/1981 | Papadofrangakis et al. | |
| 4,446,872 | 5/1984 | Marsoner et al. | |
| 4,543,826 | 10/1985 | Ferrai | 128/660 |
| 4,573,477 | 3/1986 | Namekawa | 128/663 |
| 4,598,589 | 7/1986 | Riley et al. | |
| 4,622,634 | 11/1986 | Fidel | |
| 4,622,977 | 11/1986 | Namekawa et al. | |
| 4,641,668 | 2/1987 | Namekawa | 128/663 |
| 4,660,565 | 4/1987 | Shirasaka | 128/660 |
| 4,682,229 | 7/1987 | Coates | 358/166 |
| 4,717,916 | 1/1988 | Adams | 342/107 |

OTHER PUBLICATIONS

"Systolic Time Intervals," Noninvasive Cardiology, R. P. Lewis et al., chap. 6, pp. 301–368 (1974).

Y. E. Langlois et al., "Computer Based Pattern Recognition of Carotid Artery Doppler Signals for Disease Classification: Prospective Validation," Ultrasound in Medicine and Biology, vol. 10, No. 5, pp. 581–595 (1984).

T. Spoto et al., "Microprocessor Based Real-Time Systolic Time Interval System," Proceedings of the 7th New England Bioeng. Conference, Troy, NY (Nov. 22-23, 1979) pp. 9–12.

"Real-Time Two-Dimensional Blood Flow Imaging Using an Autocorrelation Technique", by Chihiro Kasai, Koroku Namekawa, Akira Koyano, and Ryozo Omoto, IEEE Transactions on Sonics and Ultrasonics, vol. SU-32, No. 3, May 1985, pp. 458–464.

*Primary Examiner*—Jerry Smith
*Assistant Examiner*—Steven G. Kibby
*Attorney, Agent, or Firm*—Finnegan, Henderson, Farabow, Garrett & Dunner

[57] ABSTRACT

An ultrasonic imaging apparatus comprises an ultrasonic transducer for emitting an ultrasonic beam onto an interest region of a living body containing a blood flow and outputting an echo signal, a correlation circuit for determining a correlation of the signals obtained from the ultrasonic transducer and a velocity calculation circuit for calculating the velocity of the blood flow from the correlation data obtained by the correlation circuit. A zero shift process circuit zero-shifts the velocity data obtained from the velocity calculation circuit and compresses the zero-shifted velocity data in correspondance with an amount of zero shift. The zero-shifted flow velocity data is displayed within a possible display range.

10 Claims, 7 Drawing Sheets

FIG. 4A

| Address | Content |
|---|---|
| 000 | RED 1ST GRAY LEVEL |
| 001 | RED 2ND GRAY LEVEL |
| 002 | RED 3RD GRAY LEVEL |
| --- | --- |
| 07F | RED 128TH GRAY LEVEL |
| 080 | BLUE 1ST GRAY LEVEL |
| 081 | BLUE 2ND GRAY LEVEL |
| --- | --- |
| 0FD | BLUE 126TH GRAY LEVEL |
| 0FE | BLUE 127TH GRAY LEVEL |
| 0FF | BLUE 128TH GRAY LEVEL |

FIG. 4B

| Address | Content |
|---|---|
| 100 | RED 1ST GRAY LEVEL |
| 101 | RED 2ND GRAY LEVEL |
| 102 | RED 2ND GRAY LEVEL |
| --- | --- |
| 17F | RED 102ND GRAY LEVEL |
| 180 | BLUE 1ST GRAY LEVEL |
| 181 | BLUE 2ND GRAY LEVEL |
| --- | --- |
| 1DF | BLUE 77TH GRAY LEVEL |
| 1FD | RED 128TH GRAY LEVEL |
| 1FD | RED 105TH GRAY LEVEL |
| 1FE | RED 104TH GRAY LEVEL |
| 1FF | RED 103RD GRAY LEVEL |

FIG. 4C

| Address | Content |
|---|---|
| 200 | RED 1ST GRAY LEVEL |
| 201 | RED 1ST GRAY LEVEL |
| 202 | RED 2ND GRAY LEVEL |
| --- | --- |
| 27F | RED 82ND GRAY LEVEL |
| 280 | BLUE 1ST GRAY LEVEL |
| 281 | BLUE 1ST GRAY LEVEL |
| --- | --- |
| 2D4 | RED 128TH GRAY LEVEL |
| 2FD | RED 85TH GRAY LEVEL |
| 2FE | RED 84TH GRAY LEVEL |
| 2FF | RED 83RD GRAY LEVEL |

FIG. 4D

| Address | Content |
|---|---|
| 400 | RED 1ST GRAY LEVEL |
| 401 | RED 1ST GRAY LEVEL |
| 402 | RED 2ND GRAY LEVEL |
| --- | --- |
| 47F | RED 64TH GRAY LEVEL |
| 480 | RED 128TH GRAY LEVEL |
| 481 | RED 128TH GRAY LEVEL |
| --- | --- |
| 480 | RED 127TH GRAY LEVEL |
| 4FD | RED 66TH GRAY LEVEL |
| 4FE | RED 65TH GRAY LEVEL |
| 4FF | RED 65TH GRAY LEVEL |

FIG. 4E

| Address | Content |
|---|---|
| 500 | RED 1ST GRAY LEVEL |
| 501 | RED 2ND GRAY LEVEL |
| 502 | RED 2ND GRAY LEVEL |
| --- | --- |
| 57E | BLUE 104TH GRAY LEVEL |
| 57F | BLUE 103RD GRAY LEVEL |
| 580 | BLUE 1ST GRAY LEVEL |
| 581 | BLUE 2ND GRAY LEVEL |
| 582 | BLUE 2ND GRAY LEVEL |
| --- | --- |
| 5FD | BLUE 101ST GRAY LEVEL |
| 5FE | BLUE 102ND GRAY LEVEL |
| 5FF | BLUE 102ND GRAY LEVEL |

FIG. 4F

| Address | Content |
|---|---|
| 600 | RED 1ST GRAY LEVEL |
| 601 | RED 1ST GRAY LEVEL |
| 602 | RED 2ND GRAY LEVEL |
| --- | --- |
| 67E | BLUE 87TH GRAY LEVEL |
| 67F | BLUE 86TH GRAY LEVEL |
| 680 | BLUE 1ST GRAY LEVEL |
| 681 | BLUE 1ST GRAY LEVEL |
| --- | --- |
| 6FD | BLUE 84TH GRAY LEVEL |
| 6FE | BLUE 85TH GRAY LEVEL |
| 6FF | BLUE 85TH GRAY LEVEL |

FIG. 4G

| Address | Content |
|---|---|
| 800 | BLUE 128TH GRAY LEVEL |
| 801 | BLUE 128TH GRAY LEVEL |
| 802 | BLUE 127TH GRAY LEVEL |
| --- | --- |
| 87E | BLUE 65TH GRAY LEVEL |
| 87F | BLUE 65TH GRAY LEVEL |
| 880 | BLUE 1ST GRAY LEVEL |
| 881 | BLUE 1ST GRAY LEVEL |
| 882 | BLUE 2ND GRAY LEVEL |
| --- | --- |
| 8FD | BLUE 63RD GRAY LEVEL |
| 8FE | BLUE 64TH GRAY LEVEL |
| 8FF | BLUE 64TH GRAY LEVEL |

F I G. 6
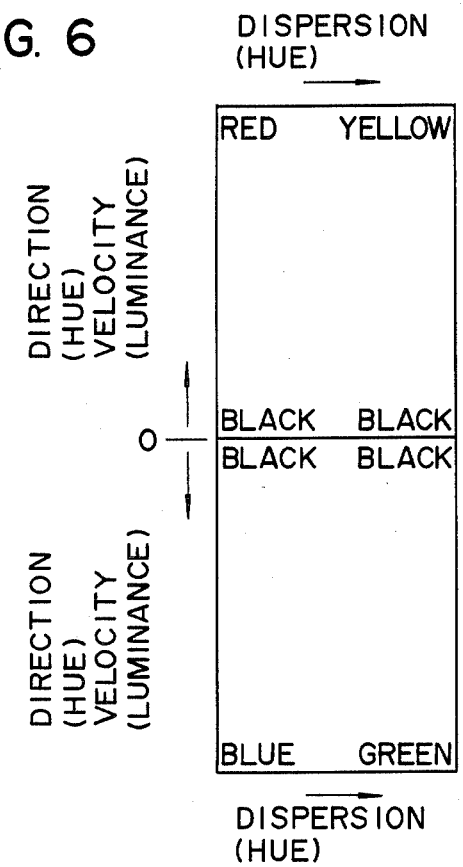
F I G. 7
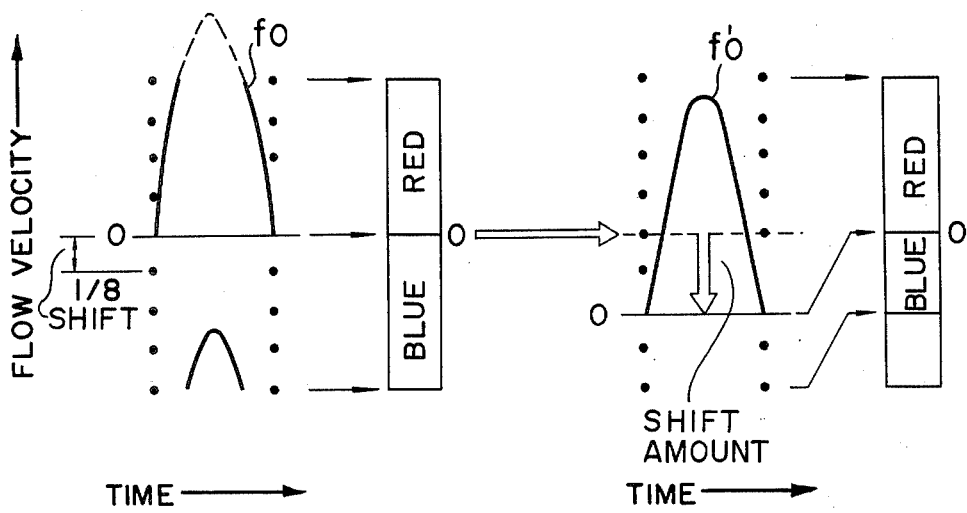

ULTRASONIC IMAGING APPARATUS FOR COLOR DISPLAY OF FLOW VELOCITY

BACKGROUND OF THE INVENTION

The present invention relates to an ultrasonic imaging apparatus and, more particularly, to an ultrasonic imaging apparatus having a color display function.

Ultrasonic imaging apparatuses are used in various fields, particularly in medicine. Ultrasonic imaging apparatuses for displaying a blood flow have been developed. These apparatuses form an image of a blood flow and can display the image in color. The image, which is a motion picture, shows the direction and flow velocity of blood flow in an object to be examined. The apparatuses, however, have functional limits, and display the image of blood flowing at a velocity exceeding a predetermined value in a color different from that used for displaying the actual blood flow velocity. In order to eliminate this drawback, an ultrasonic imaging apparatus adopting a Doppler method has been developed, which displays the result of frequency analysis at a certain point by using FFT (Fast Fourier Transform). This imaging apparatus has a funcion called zero shift or base-line shift. According to this function, when a measurement value exceeds a display limit, it is shifted downward. For example, when a blood flow velocity which changes over time exceeds the upper limit (+MAX) of the measurement range, the exceeding portion is displayed on the lower section of the display range (upper limit +MAX to lower limit −MAX), i.e., a phenomenon called aliasing occurs. Then, an operator may misunderstand the displayed image and take it for a reverse blood flow because of aliasing. In order to prevent this, the zero line of the axis of ordinate is subjected to a zero shift in order to shift the display range in the reverse flow direction. As a result, the maximum value of the flow velocity is less than the upper limit (+MAX).

In the ultrasonic imaging apparatuses, the address of a RAM corresponds to the flow velocity. When the zero shift is performed in the conventional apparatuses, data is written at an address shifted by a zero shift amount, or is read out from a memory area at an address shifted by the zero shift amount. Since a Doppler signal is sampled in synchronism with an ultrasonic rate pulse, an upper limit exists in the measurable flow velocity range, and aliasing occurs in a flow velocity component exceeding the upper limit. Aliasing in this case is expressed as a change in color of the displayed image. More specifically, assuming that forward and reverse flows are displayed in red and blue, respectively, a flow velocity component, which should originally be displayed in red and exceeds the upper limit, is displayed in blue because of aliasing. Although the operator may not mistake the aliasing portion displayed in blue as a reverse flow, it is preferably displayed in red.

According to the conventional Doppler method, the blood flow direction cannot be discriminated, unlike in blood flow imaging. Therefore, ultrasonic beams are incident from various directions, thereby finding a portion at which a maximum flow velocity can be obtained. With this method, however, since the incident directions of the ultrasonic beams cannot be arbitrarily set because of the shape of an ultrasonic probe or the positional relationship among internal organs of the patient, an error often occurs in the maximum flow velocity, depending on the ultrasonic beam incident angle. A portion at which the maximum flow velocity can be obtained must be measured while the sample volume position is adjusted, resulting in a very cumbersome operation.

SUMMARY OF THE INVENTION

It is an object of the present invention to provide an ultrasonic imaging apparatus which can easily compare an image by blood flow imaging with a Doppler signal image and discriminate a maximum flow velocity component.

According to this invention, an echo signal obtained from echo from an object to be examined is subjected to blood flow image processing and Doppler processing. A flow velocity signal is subjected to zero shift by the blood flow image processing. The zeroshifted flow velocity signal is compressed in accordance with the shift amount, and the compressed zeroshifted flow velocity signal is displayed in color within a possible display range.

BRIEF DESCRIPTION OF THE DRAWINGS

FIG. 6 shows an image by blood flow imaging; and

FIG. 7 shows a correspondence between an image by blood flow imaging and an image by a Doppler method.

DETAILED DESCRIPTION OF THE PREFERRED EMBODIMENT

Generally, when an image by blood flow imaging is displayed, a 0 line is used as a reference. The hue distribution is plotted along the axis of abscissa. The flow is plotted along the axis of ordinate. A forward flow is displayed on the plane above the 0 line, and a reverse flow is displayed on the plane below the 0 line. Changes in the blood flow direction and hue can be displayed in this format.

FIG. 7 shows the above representation method and a Doppler method. The left half of FIG. 7 shows no zero shift state and the right half thereof shows a zero shift state. When a blood flow velocity is represented by the Doppler method, if the maximum value of the blood flow velocity (f0) exceeds the ratings or performance of a TV monitor, this exceeding portion is displayed below the 0 line by aliasing, as shown in the left half of FIG. 7. When zero shift is performed, aliasing is corrected and a maximum blood flow velocity can be displayed, as shown in the right half of FIG. 7. In this case, the display range of the displayed flow velocity pattern appears to be increased. However, since the maximum value is expressed by a luminance prior to zero shift, it does not indicate a maximum flow velocity. Therefore, the display range after zero shift is compressed to the initial display range in accordance with the shift amount, and a flow velocity range represented by a single step is widened.

Figure 1:
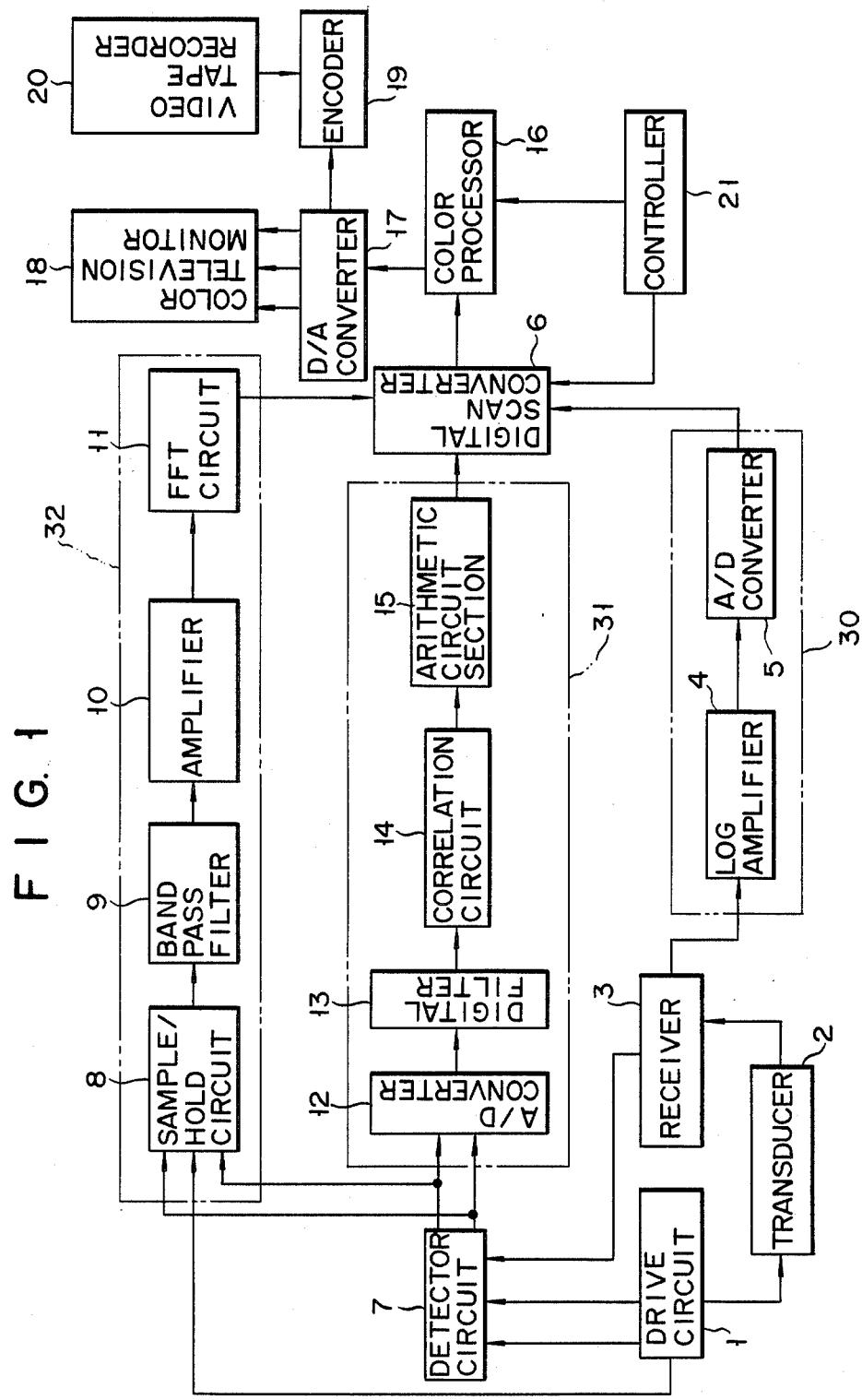
FIG. 1 is a block diagram of an ultrasonic imaging apparatus according to an embodiment of the present invention.

An embodiment for practicing the above operation will be described with reference to FIG. 1. Referring to FIG. 1, transducer 2 is driven by a drive pulse from drive circuit 1 and emits an ultrasonic beam. A beam reflected by the object, i.e., an echo wave, is converted into an echo signal by ultrasonic transducer 2. The output terminal of transducer 2 is connected to receiver 3. Receiver 3 includes a delay circuit for delaying an echo signal by a predetermined delay time and an amplifier. The output terminal of receiver 3 is connected to the input terminals of log amplifier 4 and detector circuit 7. Amplifier 4 and A/D converter 5 connected to its output terminal constitute tomographic image process circuit section 30. Section 30 outputs a B-Mode image signal.

The output terminals of detector circuit 7 are connected to blood flow imaging process section (or moving target indicator) 31 and ultrasonic Doppler process section 32. Section 31 has A/D converter 12 for converting an analog output signal of detector circuit 7 into a digital signal. The output terminal of converter 12 is connected to the input terminal of digital filter 13. Filter 13 comprises a high pass filter having a steep filtering characteristic curve for removing clutter components from a digital signal. The output terminal of filter 13 is connected to the input terminal of correlation circuit 14. The output terminal of correlation circuit 14 is connected to arithmetic circuit section 15.

Figure 2:
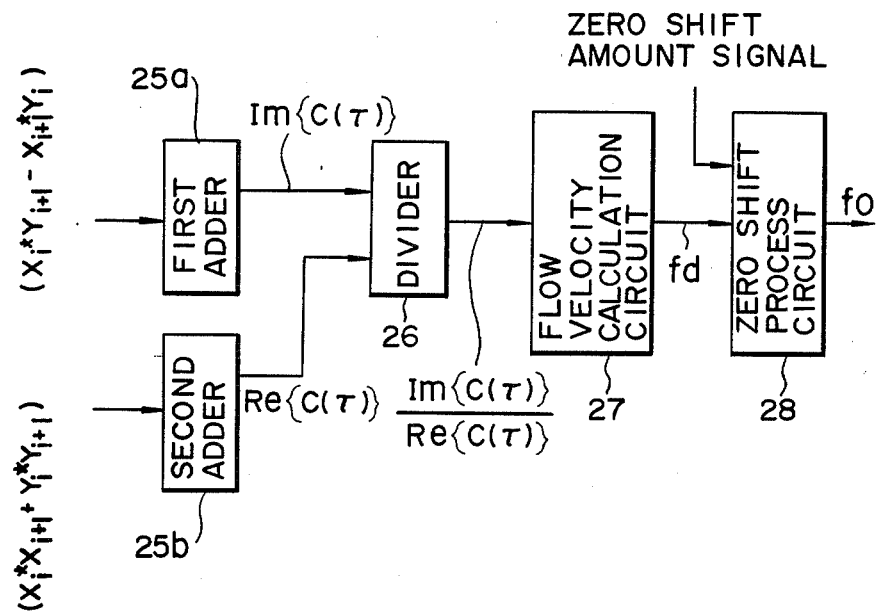
FIG. 2 is a circuit diagram of an arithmetic circuit section provided in the apparatus of FIG. 1.
Figure 3:
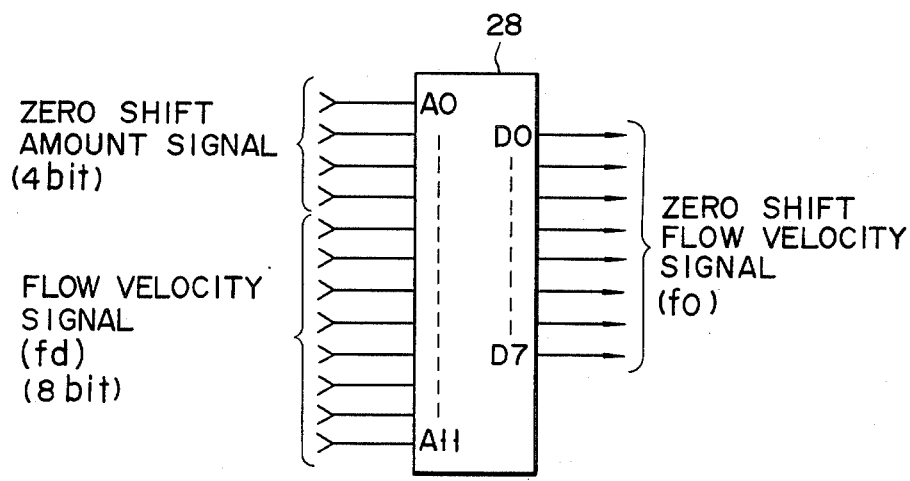
FIG. 3 shows input and output address signal lines of a zero shift process circuit provided in the circuit of FIG. 2.

Arithmetic circuit section 15 has an arrangement as shown in FIG. 2 and calculates a blood flow velocity, dispersion δ, and power P from an output signal from correlation circuit 14. More specifically, circuit section 15 has first and second adders 25a and 25b for receiving two signals from correlation circuit 14 which are phase-shifted from each other by 90 degrees. The output terminals of adders 25a and 25b are connected to the input terminals of divider 26. The output terminal of divider 26 is connected to zero shift process circuit 28.

Ultrasonic Doppler process section 32 has sample/hold circuit 8 for sampling/holding an echo signal from detector circuit 7 in synchronism with a drive signal from drive circuit 1. The output terminal of sample/hold circuit 8 is connected to band pass filter 9. Filter 9 removes any unnecessary frequency components from the output signal of circuit 8. The output terminal of filter 9 is connected to fast Fourier transform (FFT) circuit 11 through amplifier 10. FFT circuit 11 frequency-analyzes an output signal from amplifier 10 to form a Doppler signal.

The output terminals to tomographic image signal circuit 30, blood flow imaging process section 31, and ultrasonic Doppler process section 32 are connected to digital scan converter 6. The output terminal of converter 6 is connected to the input terminal of color processor 16. Color processor 16 assigns a signal (FFT digital) obtained by converter 6 to specific color data.

The output terminal of color processor 16 is connected to color television monitor 18 and encoder 19 through D/A converter 17. Encoder 19 encodes an RGB television signal from processor 16 into a composite signal and supplies the composite signal to video tape recorder 20. The timings of digital scan converter 6 and color processor 16 are controlled by controller 21.

The operation of the ultrasonic imaging apparatus having the above arrangement will be described. Drive circuit 1 supplies a drive pulse signal to ultrasonic transducer 2, and transducer 2 emits an ultrasonic beam onto the object. Then, transducer 2 receives an echo from the object and supplies an echo signal to receiver 3. Receiver 3 delays and amplifies the echo signal. The output signal from receiver 3 is input to detector circuit 7 and log amplifier 4 in tomographic image signal circuit 30.

An analog output signal from amplifier 4 is converted into a digital image signal by A/D converter 5. The digital image signal is a B-Mode image signal.

The echo signal input to detector circuit 7 is detected and input to sample/hold circuit 8 in ultrasonic Doppler process section 32 and A/D converter 12 in blood flow imaging process section 31. The sampled and held signal from sample/hold circuit 8 is input to FFT circuit 11 through band pass filter 9 and amplifier 10. FFT circuit 11 transforms the output signal from filter 9 by the fast Fourier transform, and outputs a pulse Doppler signal to scan converter 6.

An analog detection signal is converted into a digital signal by A/D converter 12, filtered by digital filter 13, and input to correlation circuit 14. Correlation circuit 14 calculates a correlation among echo signals obtained by steering of ultrasonic beams by several times (10 to 16), and supplies an obtained output to arithmetic circuit section 15.

In arithmetic circuit section 15, two signals obtained by correlation calculation, i.e., $(X_i \cdot Y_{i+1} - X_{i+1} \cdot Y_i)$ and $(X_i \cdot X_{i+1} + Y_i \cdot Y_{i+1})$ are input to first and second adders 25a and 25b, as shown in FIG. 2, and imaginary and real part signals $Im\{C(\tau)\}$ and $Re\{C(\tau)\}$ are output. Signals $Im\{C(\tau)\}$ and $Re\{C(\tau)\}$ are input to divider 26, and divider 26 performs calculation $Im\{C(\tau)\}/Re\{C(\tau)\}$. The quotient of division is input to flow velocity calculation circuit 27. Calculation circuit 27 calculates flow velocity fd in accordance with following equation:

$$fd = fr/2\pi \tan^{-1}[Im\{C(\tau)\}/Re\{C(\tau)\}] \qquad (1)$$

Output signal fd of calculation circuit 27 is input to zero shift process circuit 28. Process circuit 28 receives a zero shift amount signal (4 bits) from an input means (not shown) and flow velocity signal fd (8 bits) and outputs zero shift flow velocity signal f0. Process circuit 28 comprises, e.g., a ROM in practice. In process circuit 28, a reference level, i.e., a black level is defined as 0. Process circuit 28 stores zero shift data corresponding to ⅛, 2/8, and ⅜ shift amounts from the 0 level toward the blue direction, and ⅛, 2/8, ⅜, and 4/8 shift amounts from the 0 level toward the red direction, as shown in FIGS. 4A to 4G.

Figure 4:
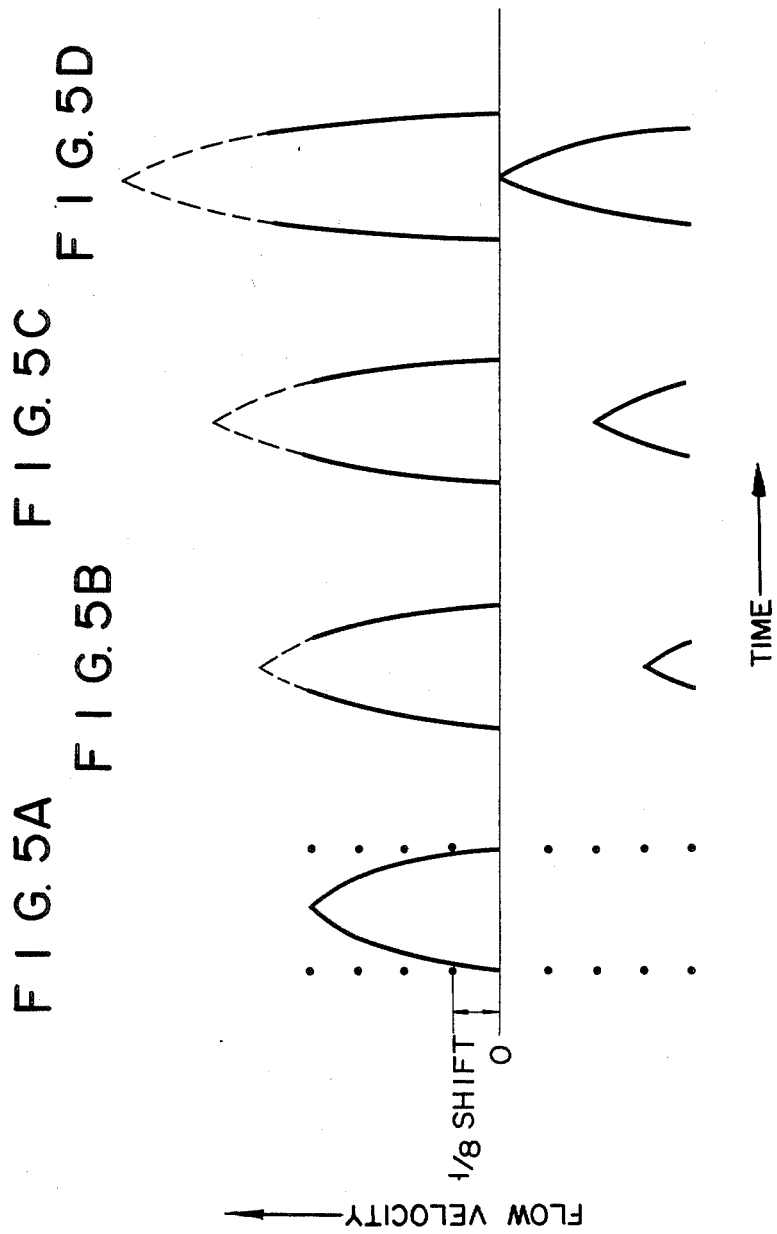
FIGS. 4A to 4G show gray scale patterns stored in the zero shift process circuit.
Figure 5:
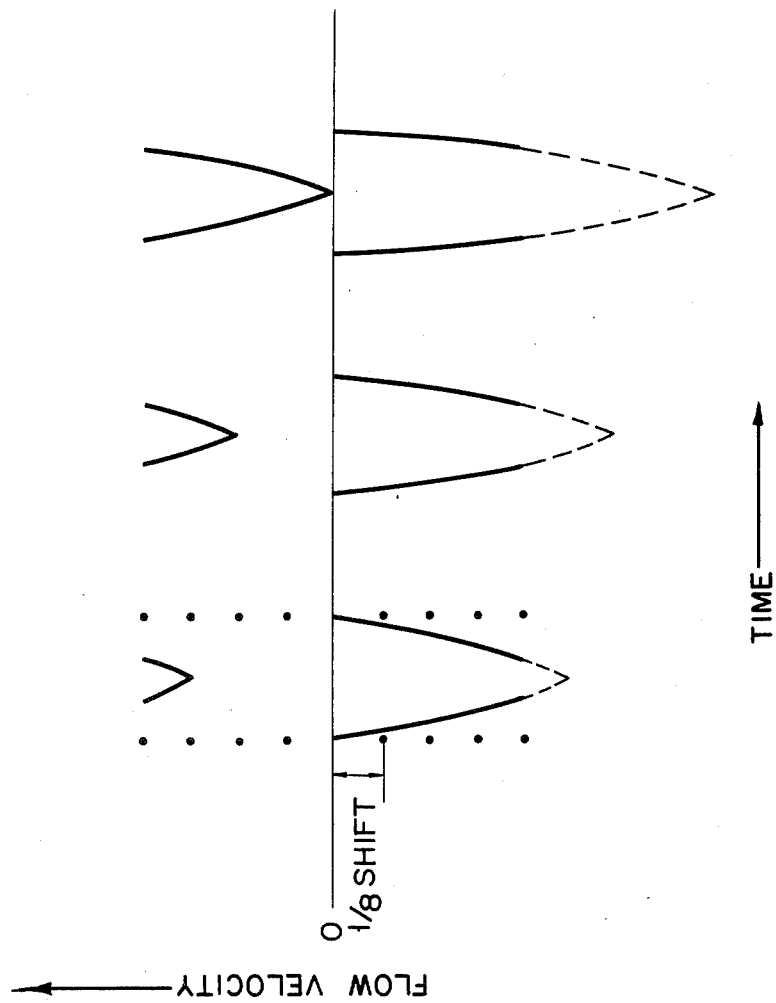
FIGS. 5A to 5G show FFT representations corresponding to the gray scale patterns of FIGS. 4A to 4G.

FIG. 4A shows zero shift data whose shift amount is 0. In this case, color data of red 1st to 128th gray levels are sequentially assigned to addresses 000 to 07F, and color data of blue 1st to 128th gray levels are sequentially assigned to addresses 080 to 0FF. When these memory contents are indicated in terms of FFT representations, they correspond to the components which are not zero-shifted in FIG. 5A.

The zero shift data shown in FIG. 4B represents shift amount ⅛ toward the blue direction. In this case, color data representing red 1st gray level to red 102nd gray level are sequentially assigned to addresses 100 to 17F, and a red aliasing component, i.e., red 103rd gray level to red 128th gray level are stored to addresses 1DF to 1FF in the reverse order. Color data representing blue 1st gray level to blue 77th gray level are sequentially assigned to addressed 180 to 1DE. When the memory contents in this case are displayed by FFT representation, they correspond to components which are not zero-shifted in FIG. 5B. Similarly, the memory contents concerning zero shift amounts ⅛, 2/8, and 4/8 are shown in FIGS. 4C and 4C and correspond to the FFT representations of FIGS. 5C and 5D.

FIGS. 4E to 4G show memory contents respectively corresponding to the shift amounts ⅛, 2/8, and 4/8 in a case of zero shift toward the red direction. These memory contents correspond to the FFT representations of FIGS. 5E to 5G. As is apparent from the drawings, when the shift amount is 4/8, the memory stores gray scale data of either red or blue.

Assume that an operator inputs a zero shift signal of 2/8 shift toward the blue direction as a zero shift amount signal through an input means. Then, zero shift process circuit 28 selects a gray scale pattern shown in FIG. 4C. In this pattern, addresses 200 and 201, which represent two gray levels in the case of no zero shift, represent one gray level. Namely, the range indicated by flow velocity signal fd is more compressed, compared to the case of no zero shift. It must be noted that, in the case of 2/8 zero shift, all flow velocity signals at the two adjacent addresses do not always represent one gray level, and the signal at each address representing one gray level can also be included in the memory contents in FIG. 4C.

Gray scale (FIG. 4C) pattern data is subjected to zero shift by 2/8, and is read out from the ROM in zero shift process circuit 28 as zero shift flow velocity signal f0 which causes no aliasing. In this case, data representing 1st to 82nd gray levels assigned to addresses 200 to 27F and data representing 83rd to 128th gray levels assigned to addresses 2FF to 2D4 are supplied to digital scan converter 6 as flow velocity signal 0. At this time, a Doppler signal from FFT circuit 11 in Doppler processor section 32 is read in scan converter 6. Scan converter 6 supplies this Doppler signal and flow velocity signal f0 to color processor 16. In this case, the Doppler signal is shifted in accordance with the zero shift amount of zero shift flow velocity signal f0 and is read out from converter 6.

Color processor 16 converts flow velocity signal f0 into a color signal, and supplies the same to color television monitor 18 through D/A converter 17 together with the Doppler signal. Monitor 18 displays the corresponding color and Doppler signal images representing zero shift flow velocity signal f0.

Following the same procedures as described above, the gray scale patterns are selected in accordance with the zero shift amounts, i.e., shift amounts ⅛ and ⅜ toward the blue direction, and ⅛, 2/8, ⅜, and 4/8 toward the red direction, thereby displaying a zero shift flow velocity signal free from aliasing.

The Doppler signal of FFT circuit 11 can be read out from scan converter 6 independently from zero shift flow velocity signal f0 of zero shift process circuit 28 by controlling addressing using controller 21.

The zero shift process circuit may be arranged such that flow velocity signal fd obtained by velocity flow calculation circuit 27 can be read out by digital scan converter 6, and that flow velocity signal fd can be subjected to zero shift.

Flow velocity calculation circuit 27 may be omitted. In this case, flow velocity signal fd may be obtained by an arithmetic calculation in advance, and a ROM, which can read out a zero shift flow velocity signal in response to the calculated data as an address signal, may be provided in zero shift process circuit 28.

What is claimed is:

1. An ultrasonic imaging apparatus comprising:
   ultrasonic transducer means for emitting an ultrasonic beam onto an object containing flow materials and for converting echoes of said beam from the object into echo signals;
   calculation means for processing the echo signals output from said ultrasonic transducer means, for calculating a velocity of the flow materials from said echo signals, and for outputting a velocity signal corresponding to the calculated velocity;
   zero shift means for zero-shifting, by a predetermined shift amount, the velocity signal output from said calculation means to produce a zero-shifted velocity signal; and
   means for displaying in one of a plurality of color levels the zero-shifted velocity signal output from said zero shift means;
   wherein at times when the velocity of the flow materials in one direction exceeds a display limit, the velocity signal corresponds to another velocity of the flow materials in an opposite direction within the display limit, and the production of the zero-shifted velocity signal prevents the display of a color level corresponding to said another velocity in the opposite direction.

2. An apparatus according to claim 1, wherein said calculation means comprises correlation means for determining a correlation among the echo signals processed by said calculation means and for outputting a correlation signal, and means for calculating the velocity of the flow materials from the correlation signal output from said correlation means.

3. An apparatus according to claim 1, wherein said zero shift means comprises means for generating a zero shift amount signal for designating the zero shift amount, and a ROM which stores color data corresponding to a plurality of velocities of the flow materials which is accessed by the velocity signal and the zero shift amount signal, wherein the color data accessed from the ROM in response to the zero shift amount signal when the velocity of the flow materials in one direction exceeds a display limit is not the color data corresponding to said another velocity of the flow materials in the opposite direction within the display limit.

4. An ultrasonic imaging apparatus comprising:
   ultrasonic transducer means for emitting an ultrasonic beam onto a region of interest of a living body containing a blood flow and for converting echoes of said beam from the object into echo signals;
   Doppler processing means coupled to said ultrasonic transducer means for fast-Fourier transforming the echo signals to produce Doppler data;
   tomograph signal output means coupled to said transducer means for processing the echo signals and outputting tomographic image data;
   calculation means for processing the echo signals output from said ultrasonic transducer means, for calculating a velocity of the blood flow from the echo signals, and for outputting velocity data;
   shift data means for selectively producing shift data corresponding to one of a plurality of shift amounts;
   zero shift means for zero-shifting the velocity data output from said calculation means in accordance with the shift data produced from said shift data means to produce zero-shifted velocity data, for compressing the zero-shifted velocity data in accordance with the shift amount, and for outputting the compressed zero-shifted velocity data;

a digital scan converter for receiving the Doppler data, the compressed zero-shifted velocity data, and the tomographic image data, and for selectively outputting the Doppler, compressed zero-shifted velocity, and tomographic image data; and means for displaying in one of a plurality of color levels the compressed zero-shifted velocity data from said digital scan converter, wherein the plurality of color levels corresponds to a first range of velocities of the blood flow for zero-shifted velocity data and corresponds to a second range of velocities wider than the first range for compressed zero-shifted velocity data;

wherein at times when the velocity of the blood flow in one direction exceeds a display limit, the velocity data corresponds to another velocity of the blood flow in an opposite direction within the display limit, and the output of compressed zero-shifted velocity data prevents the display of a color level corresponding to said another velocity in the opposite direction.

5. An ultrasonic imaging apparatus according to claim 4, wherein said calculation means includes means for determining a correlation of the processed echo signals, and means for calculating the velocity from the correlation obtained by said correlation-determining means.

6. An ultrasonic imaging apparatus according to claim 4, wherein said zero shift means includes a read-only memory (ROM) storing color data corresponding to a plurality of velocities of the blood flow and accessed by the velocity data and the shift data, wherein the color data accessed from the ROM in response to the shift data when the velocity of the blood flow in one direction exceeds a display limit is not the color data corresponding to said another velocity of the blood flow in the opposite direction within the display limit.

7. An ultrasonic imaging apparatus according to claim 4, wherein said displaying means is means for displaying the tomographic image data and at least one of the Doppler data and the velocity data.

8. An ultrasonic imaging apparatus according to claim 4, wherein the displaying means includes color processor means for assigning specific color levels to input data, and wherein said scan converter includes means for inputting both the velocity data and Doppler data as input data to said color processor means.

9. An ultrasonic imaging apparatus according to claim 4, wherein said zero shift means includes means for storing first color data representing a plurality of levels of a first color corresponding to a plurality of velocities of the blood flow and indicating a forward blood flow direction, and second color data representing a plurality of levels of a second color corresponding to a plurality of velocities of the blood flow and indicating a reversed blood flow direction, and means for accessing the color data stored in said storing means in response to the shift data representing the shift amount and the velocity data.

10. An ultrasonic imaging apparatus according to claim 9, wherein said storing means includes a memory area having a plurality of addresses corresponding to a plurality of levels of the first and second colors, and wherein at least one group of addresses in the plurality of addresses includes at least two addresses that each store color data representing the same color level, wherein a greater range of velocities of the blood flow corresponds to a color level represented by color data stored in at least two addresses.

* * * * *